United States Patent [19]

Goff et al.

[11] Patent Number: 5,256,554
[45] Date of Patent: Oct. 26, 1993

[54] EXPRESSION OF HUMAN IMMUNODEFICIENCY VIRUS (HIV) REVERSE TRANSCRIPTASE

[75] Inventors: Stephen P. Goff, Tenafly, N.J.; Naoko Tanese, New York, N.Y.; William A. Haseltine, Cambridge, Mass.

[73] Assignees: The Trustees of Columbia University in the City of New York, New York, N.Y.; The Dana Farber Cancer Institute, Boston, Mass.

[21] Appl. No.: 800,682

[22] Filed: Dec. 2, 1991

Related U.S. Application Data

[63] Continuation of Ser. No. 552,848, Jul. 12, 1990, abandoned, which is a continuation of Ser. No. 865,156, May 20, 1986, abandoned.

[51] Int. Cl.$^5$ .................. C12N 9/00; C12N 15/49
[52] U.S. Cl. .................. 435/183; 435/974; 930/221; 935/33; 935/38; 935/40; 935/47; 935/73
[58] Field of Search ............ 435/172.3, 320.1, 69.1, 435/183

[56] References Cited

U.S. PATENT DOCUMENTS

| 4,387,162 | 6/1983 | Aigle et al. | 435/320.1 X |
| 4,487,835 | 12/1984 | Uhlin et al. | 435/320.1 X |
| 4,663,290 | 5/1987 | Weis et al. | 935/14 X |

FOREIGN PATENT DOCUMENTS

WO8400380 2/1984 World Int. Prop. O.

OTHER PUBLICATIONS

N. Tanese et al. (1988) DNA 7(6):407–416.
C. H. Schein et al. (1988) Bio/Technology 6:291–294.
H. F. Seow et al. (1989) Bio/Technology I:363–368.
A. D. Hoffman et al. (1985) Virology 147:326–335.
Tacon, W. et al., Molec. Gen. Genet., vol. 177, pp. 427–438, 1980.
Tanese, N. et al., Proc. Natl. Acad. Sci., vol. 82, pp. 4944–4948, Aug., 1985.
Chang, N. et al., Science, vol. 228, pp. 93–96, Apr., 1985.
Ratner, L. et al., Nature, vol. 313, pp. 277–284, Jan., 1985.
Wain–Hobson, et al., Cell, vol. 40, pp. 9–17, Jan. 1985.
Muesing, M. et al., Nature, vol. 313, pp. 450–458, Feb., 1985.
Farmerie, W. et al., Science, vol. 236, pp. 305–308, Apr., 1987.
Tanese, N. et al., J. Virology, vol. 59, pp. 743–745, Sep., 1986.

Primary Examiner—Richard A. Schwartz
Assistant Examiner—Johnny F. Railey II
Attorney, Agent, or Firm—John P. White

[57] ABSTRACT

This invention describes pHRT25, a plasmid containing a modified pol gene of the Human Immunodeficiency Virus Type 1 (HIV-1), formerly HTLV-III, under control of an inducible trp promoter. Methods of expressing reverse transcriptase activity using pHRT25 in E. coli are described.

1 Claim, 26 Drawing Sheets

FIGURE 4A

| CLONE | | NUCLEOTIDE POSITION |
|---|---|---|
| | -----US | |
| | IR | |
| BH10 | TGGAACGGCTAATTCACTCCCAACGAAGACAAGA | -420 |
| BH8 | ---------------------------------- | |
| BH10 | TATCCTTGATCTGTGGATCTACCACACACAAGGCTACTTCCCTGATTAGCAGAACTACACACAGGGCCAGGAT | -345 |
| | (Bam HI) | |
| BH8 | ----------------C--------------------------------------------------AG-- | |
| BH10 | CAGATATCCACTGACCTTTGGATGTGGTCTACAAGTAGTAGTACCAGTTGAGCCAGAGAAGTTAGAAGAAGCCAACA | -270 |
| BH8 | ---------------------------------------G-------------------T------------- | |
| BH10 | AGGAGAGAACACCAGCTTGTTACACCCTGTGAGCCTGCATGGAATGATGACCCGGAGAGAGAAGTGTTAGAGTG | -195 |
| BH8 | ---------------------A-----------------------T------------------- | |
| BH10 | GAGGTTTGACAGCCGCCTAGCATTCATCACATGGCCCAGAGCTGCATCCGGAGTACTTCAAGAACTGCTGACA | -120 |
| BH8 | -------------------------------------------------------------T-- | |
| BH10 | TCGAGCTTGCTACAAGGGACTTTCCGCTGGGGACTTTCCAGGAGGCGTGGCCTGGGCGGGACTGGGG | -45 |
| BH8 | ------------------------------------------------------------------ | |
| | TATA | |
| | BOX Pvu II US--- | |
| BH10 | AGCCCTCAGATCCTGCATATAAGCAGCTGCTTTTTGCCTGTACT | -0 |
| BH8 | -------------------------------------------- | |

FIGURE 4B

```
                I--R            Bal II      Sst I
        BH10    GGGTCTCTCTGGTTAGACCAGATCTGAGCCTGGGAGCTC                                    39
        BH8     --------------------------------------

HXB2                                          TCTGGCTAACTAGGGAACCCACTGCTTAAGCCTCAA  75

Hind III     R----1----US
        HXB2    TAAAGCTTGCCTTGAGTGCTTCAAGTAGTGTGTGCCCGTCTGTTGTGTGACTCTGGTAACTAGAGATCCCTCAGA  150
                                                     US--1--tRNA-lysine----1 ---Leader sequence
                                     IR
        HXB2    CCCTTTTAGTCAGTGTGGAAAATCTCTAGCAGTGGCGCCCGAACAGGGACCTGAAAGCGAAAGGGAAACCA    221

Sst I
        HXB2    GAGCTCTCTCGACGCAGGACTCGGCTTGCTGAAGCGCGCACGGCAAGAGGCGAGGGGCGGCGACTGGTGAGTACG  296
        BH5     ---------------------------------------------------------------------------

Leader sequence--1--GAG p17
        BH10    CCAAAAATTTTGACTAGCGGAGGCTAGAAGGAGAGAGATGGGTGCGAGAGCGTCAGTATTAAGCGGGGGAGAATT  371
        BH5     ---------------------------------------------------------------------------
                                                        MetGlyAlaArgAlaSerValLeuSerGlyGlyGluLeu BH10    AGATCGATGGGAAAAATTCGGTTAAGGCCAGGGGGAAAGAAAAAATATAAATTAAAACATATAGTATGGGCAAG   446
        BH5     --------------------------------------------------------------------------
                AspArgTrpGlyGluLysIleArgLeuArgProGlyLysLysLysTrpLysLysHisIleValTrpAlaSer
```

FIGURE 4C

```
BH10   CAGGGAGCTAGAACGATTCGCAGTTAATCCTGGCCTGTTAGAAACATCAGAAGGCTGTAGACAAATACTGGACA      521
       ArgGluLeuGluArgPheAlaValAsnProGlyLeuLeuGluThrSerGluGlyCysArgGlnIleLeuGlyGln
BH5    ------------------------------------------------------------------------

BH10   GCTACAACCATCCCTTCAGACAGGATCAGAAGAACTTACATCATTATATAATACAGTAGCAACCCTCTATTGTGT      596
       LeuGlnProSerLeuGlnThrGlySerGluGluLeuHisHisTyrTyrThrValAlaThrLeuTyrCysVal
BH5    ------------------------------------------------------------------------
                                      Hind III BH10   GCATCAAAGGATAGAGATAAAAGACACCAAGGAAGCTTTAGACAAGATAGAGGAAGAGCAAAACAAAAGTAAGAA      671
       HisGlnArgIleGluIleLysAspThrLysGluAlaLeuAspLysIleGluGluGlnAsnLysSerLysLys
BH5    ------------------------------------------------------------------------
                Pvu II                              GAG p17----¦----GAG p24

BH10   AAAGCACAGCAAGCAGCAGCTGACACAGGACACAGCAGTCAGGTCAGCCAAATTACCCTATAGTGCAGAACAT      746
       LysAlaGlnGlnAlaAlaAlaAlaAspThrGlyHisSerSerGlnValSerGlnLeuProTyrSerArgThrCys
BH5    ------------------------------------------------------------------------
                                      Aha III

BH10   CCAGGGGCAAATGGTACATCAGGCCATATCACCTAGAACTTTAAATGCATGGGTAAAAGTAGTAGAAGAGAAGGC      821
       GlnGlyGlnMetValHisGlnAlaIleSerProArgThrLeuAsnAlaTrpValLysValValGluGluLysAla
BH5    ------------------------------------------------------------------------
                                                                    Aha III

BH10   TTTCAGCCCAGAAGTAATACCCATGTTTTCAGCATTATCAGAAGGAGCCACCCCACAAGATTTAAACACCATGCT      896
       PheSerProGluValIleProMetPheSerAlaLeuSerGluGlyAlaThrProGlnAspLeuAsnThrMetLeu
BH5    -----------------------G------------------------------------------------
```

FIGURE 4D

```
                                                                    Pst I
BH10  AAACACAGTGGGGGACATCAAGCAGCCATGCAAATGTTAAAAGAGACCATCAATGAGGAAGCTGCAGAATGGGA    971
      AsnThrValGlyGlyHisGlnAlaAlaMetGlnMetLeuLysGluThrIleAsnGluGluAlaAlaGluTrpAsp
BH5   ----------------------------------------------------------------------

BH10  TAGAGTACATCCAGTGCATGCAGGGCCTATTGCACCAGGCCAGATGAGAGAACCAAGGGAAGTGACATAGCAGG   1046
      ArgValHisProValHisAlaGlyProIleAlaGlyProGlnMetArgGlyGlySerAspIleAlaGly
BH5   -----G----------------------C-----------------------------------------

BH10  AACTACTAGTACCCTTCAGGAACAAATAATCCACCTATCCCAGTAGGAGAAATTTATAA                 1121
      ThrThrSerThrLeuGlnGluGlnIleIleGlyTrpMetThrAsnAsnProProIleProValGlyGluIleTyrLys
BH5   ----------------------------------------------------------------------

BH10  AAGATGGATAATCCTGGGATTAAATAAAATAGTAAGAATGTATAGCCCTACCAGCATTCTGGACATAAGACAAGG   1196
      ArgTrpIleIleLeuGlyLeuAsnLysIleValAlaArgMetTyrSerProThrSerIleLeuAspIleArgGlnGly
BH5   -------------------------------G--------------------T------------------

Hind III
BH10  ACCAAAAGAACCTTTTAGAGACTATGTAGACCGGTTCTATAAAACTCTAAGAGCCGAGCAAGCTTCACAGAGGAGT   1271
      ProLysGluProPheArgAspTyrValAspArgPheTyrLysThrLeuArgAlaGluGlnAlaSerGlnGluVal
BH5   -----G------------C-------------------------------------------------A---

Aha III
BH10  AAAAATTGGATGACAGAAACCTTGTTGGTCCAAAATGCGAACCCAGATTGTAAGACTATTTTAAAAGCATTGGG    1346
      LysAsnTrpMetThrGluThrLeuLeuValGlnAsnAlaAsnProAspCysLysThrIleLeuAlaLeuGly
BH5   ----------------------------------------------------------------------
```

FIGURE 4E

```
BH10  ACCAGGCGGCTACACTAGAAGAAATGATGACAGCATGTCAGGGAGTAGAGGAGACCCGGCCATAAGGCAAGAGTTTT  1421
          ProAlaAlaThrLeuGluGluMetMetThrAlaCysGlnGlyValGlyProGlyHisLysLysAlaArgValLeu
BH5   ----------------------------------------------------------------------------

BH10  GGCTGAAGCAATGAGCCAAGTAACAAATACAGCTACCATAATGATGCAGAGAGGCAATTTTAGGAACCAAAGAAA  1496
          AlaGluAlaMetSerGlnValThrAsnThrAlaThrIleMetMetGlnArgGlyAsnPheArgAsnGlnArgLys
BH5   -----------------T--A-------------------A-----------------------------------
                              SerThr
                             ------Direct Repeat------

BH10  GATGGTTAAGTGTTTCAATTGTGGCAAAGAAGGGCACACAGCCAGAAATTGCAGGGCCCCTAGAAAAGGGCTG  1571
          MetValLysCysPheAsnCysGlyLysGluGlyHisThrAlaArgAsnCysArgAlaProArgLysGlyCys
BH5   A--T-----------------------------T--A------------A--------------GA----------
                                          Ile              Lys

BH10  TTGGAAATGTGGAAAGGAAGGACACCAAATGAAAGATTGTACTGAGAGACAGGCTAATTTTTTAGGGAAGATCTG  1646
          TrpLysCysGlyLysGluGlyHisGlyGluArgGlnAlaAsnPheLeuGlyLysIleTrp
                  ---POL                              Arg    Bal II
                                                      PhePheArgGluAspLeu
BH5   ----------------------------------------------------------------------------

BH10  GCCTTCCTACAAGGGAAGGCCAGGGAATTTTCTTCAGAGACCAGAGCCAACAGCCCCACCATTCTTCAGAG  1721
          ProSerTyrLysGlyArgProGlyAsnPheLeuGlnSerArgProGluProThrAlaProProPheLeuGlnSer
          AlaPheLeuGlnGlyLysAlaArgGluPheSerSerGluGlnThrArgAlaAsnSerProThrIleSerSerGlu
                                                                    ------Direct
BH5   ----------------------------------------------------------------------------
```

FIGURE 4F

```
              Repeat----------
BH10   CAGACCAGAGCCAACAGCCCCACCAGAAGAGAGCTTCAGGTCTGGGTAGAGACAACAACTCCCCCTCAGAAGCA       1796
       ArgProGluProThrAlaProProGluSerPheArgSerGlyValGluThrThrProProGlnLysGln
       GlnThrArgAlaAsnSerProThrArgArgGluLeuGlnValTrpGlyArgAspAsnAsnSerProSerGluAla
BH5    ---------------------------------T-------------------------------
                                        Ser
                                        Leu
                                        GAG p15-------

BH10   GGAGCCGATAGACAAGGAACTGTATCCTTTAACTTCCCTCAGATCACTCTTTGGCAACGACCCCCTCGTCACAATA       1871
       GluProIleAspLysGluLeuTyrProLeuThrSerLeuArgSerLeuPheGlyAsnAspProSerSerGln
       GlyAlaAspArgGlnGlyThrValSerPheAsnPheProGlnIleThrLeuTrpGlnArgProLeuValThrIle
BH5    ---------------------------------------------------------------

BH10   AAGATAGGGGGGCAACTAAAGGAAGCTCTATTAGATACAGGAGCAGATGATACAGTATTAGAAGAAATGAGTTTG       1946
       LysIleGlyGlyGlnLeuLysGluAlaLeuLeuAspThrGlyAlaAlaAspAspThrValLeuGluGluMetSerLeu
BH5    ---------------------------------------------------------------

BH10   CCAGGAAGATGGAAACCAAAAATGATAGGGGGAATTGGAGGTTTTATCAAAGTAAGACAGTATGATCAGATACTC       2021
       ProGlyArgTrpLysProLysMetIleGlyGlyIleGlyGlyPheIleLysValArgGlnTyrAspGlnIleLeu
BH5    ---------------------------------------------------------------

BH10   ATAGAAATCTGTGGACATAAAGCTATAGGTACAGTATTAGTAGGACCTACACCTGTCAACATAATTGGAAGAAAT       2096
       IleGluIleCysGlyHisLysAlaIleGlyThrValLeuValGlyProThrProValAsnIleIleGlyArgAsn
BH5    ---------------------------------------------------------------
```

FIGURE 4G

```
              Aha III
BH10  CTGTTGACTCAGATTGGTTGCACTTTAAATTTTCCCATTAGCCCTATTGAGACTGTACCAGTAAAATTAAAGCCA      2171
      LeuLeuThrGlnIleGlyCysThrLeuAsnPheProIleSerProIleGluThrValProValLysLeuLysPro
BH5   ----------------------------T-------------A---------

BH10  GGAATGATGGCCCAAAGTTAAACAATGGCCATTGACAGAAGAAAATAAAGCATTAGTAGAAATTTGTACA          2246
      GlyMetAspGlyProLysValLysGlnTrpProLeuThrGluGluLysIleLeuLysAlaLeuValGluIleCysThr
BH5   ------------------------T-----------

BH10  GAAATGGAAAGGAAGGAAAAATTCAAAAATTGGGCCTGAGAATCCATACAATACTCCAGTATTGCCATAAAG        2321
      GluMetGluArgLysGluLysIleGlnLysLeuValGlyLeuGluAsnProTyrAsnThrProValLeuAlaIleLys
BH5   ----------A-----------

BH10  AAAAAGACAGTACTAAATGGAGAAAATTAGAGATTTCAGAGAACTTAATAAGAGAACTCAAGACTTCTGGGAA        2396
      LysLysAspSerThrLysTrpArgLysLeuValAspPheArgLysLeuAsnLysArgThrGlnAspPheTrpGlu
BH5   ---------------------------G----------
                                 Arg

BH10  GTTCAATTAGGAATACCACATCCCGCAGGGTTAAAAAGAAAAATCAGTAACAGTACTGGATGTGGGTGATGCA       2471
      ValGlnLeuGlyIleProHisProAlaGlyLeuLysLysLysLysSerValThrValLeuAspValGlyAspAla
BH5   --------------G---------

BH10  TATTTTTCAGTTCCCTTAGATGAAGACTTCAGGAAGTATACTGCATTACCATACTAGTATAAACAATGAGACA        2546
      TyrPheSerValProLeuAspGluAspPheArgLysTyrThrAlaPheThrIleProSerIleAsnAsnGluThr
BH5   ---------T----
      SerGly
```

FIGURE 4H

```
BH10  CCAGGGATTAGATATCAGTACAATGTGCTTCCACAGGATGGAAAGGATCACCAGCAATATTCCAAGTAGCATG    2621
      ProGlyIleArgTyrGlnTyrAsnValLeuProGlnGlyTrpLysGlySerProAlaIlePheGlnSerSerMet
BH5   ------G-G-----------------------------------------------------------
            SerGly
                     Aha III
BH10  ACAAAATCTTAGAGCCTTTAAAAACAAATCCAGACATAGTATCTATCAATACATGATGATTTGTATGTA    2696
      ThrLysIleLeuGluProPheLysLysGlnAsnProAspIleValIleTyrGlnTyrMetAspLeuTyrVal
BH5   -------------------------G-----------T------------------------------
                               Arg

BH10  GGATCTGACTTAGAATAGGGCAGCATAGAACAAAATAGAGGAGCTGAGACAACATCTGTTGAGGTGGGACTT    2771
      GlySerAspLeuGluIleGlyGlnHisArgThrLysIleGluGluLeuArgGlnHisLeuLeuLeuArgTrpGlyLeu
BH5   ----------------------------------------------------------------T---
                                                                      Phe

BH10  ACCACCACCAGACAAAAACATCAGAAAGAACCTCCATTCCTTGGATGGGTTATGAACTCCATCCTGATAAATGG    2846
      ThrThrProAspLysLysHisGlnLysGluProProPheLeuTrpMetGlyTyrGluLeuHisProAspLysTrp
BH5   ----------------------------------------------------------------------
                                Pvu II
BH10  ACAGTACAGCCTATAGTGCTGCCAGAAAAAGACAGCTGGACTGTCAATGACATACAGAAGTTAGTGGGAAATTG    2921
      ThrValGlnProIleValLeuProGluLysAspSerTrpThrValAsnAspIleGlnLysLeuValGlyLysLeuLeu
BH5   ---GA-----------------------------------------------------A-----------
         Ile

BH10  AATTGGGCAAGTCAGATTTACCCAGGGATTAAAGTAAGGCAATTATGTAAACTCCTTAGAGGAACCAAGCACTA    2996
      AsnTrpAlaSerGlnIleTyrProGlyIleLysValArgGlnLeuCysLysLeuLeuArgGlyThrLysAlaLeu
BH5   ----------------T-----------------------------------------------------
```

FIGURE 4I

```
BH10  ACAGAAGTAATACCACTAACAGAAGAGCAGAGCTAGAACTGGCAGAAAACAGAGAGATTCTAAAGAACCAGTA   3071
      ThrGluValIleProLeuThrGluGluAlaGluLeuAlaGluLeuAsnArgGluIleLeuLysGluProVal
BH5   ----------------------------------------------------------------

BH10  CATGGAGTGTATTATGACCCATCAAAAGACTTAATAGCAGAAATACAGAAGCAGGGCAAGGCCAATGACATAT   3146
      HisGlyValValTyrTyrAspProSerLysAspLeuIleAlaGluIleGlnLysGlnGlyGlnGlyGlnTrpThrTyr
BH5   ----------------------------------------------------------------

Aha III
BH10  CAAATTTATCAAGAGCCATTTAAAATCTGAAAACAGGAAAATATGCAAGAATGAGGGGTGCCCACACTAATGAT   3221
      GlnIleTyrGlnGluProPheLysAsnLeuLysThrGlyLysTyrAlaArgMetArgGlyAlaHisThrAsnAsp
BH5   ----------------------------------------------------------------

Aha III
BH10  GTAAAACAATTAACAGAGGCAGTGCAAAAATAACCACAGAAAGCATAGTAATATGGGGAAAGACTCCTAAATTT   3296
      ValLysGlnLeuThrGluAlaValGlnLysIleThrThrGluSerIleValIleTrpGlyLysThrProLysPhe
BH5   ----------------------------------------------------------------

BH10  AAACTACCCATACAAAAGGAAACATGGGAAACATGTGGACAGAGTATTGGCAAGCCACCTGGATTCCTGAGTGG   3371
      LysLeuProIleGlnLysGluThrTrpGluThrTrpTrpThrGluTyrTrpGlnAlaThrTrpIleProGluTrp
BH5   ----A-----------------------------------------------------------

Kpn I
BH10  GAGTTTGTTAATACCCCTCCTTTAGTGAAATTATGGTACCAGTTAGAGAAAGAACCCATAGTAGGAGCAGAAACC   3446
      GluPheValAsnThrProProLeuValLysLeuTrpTyrGlnLeuGluLysGluProIleValGlyAlaGluThr
BH5   ----------------------------------------------------------------
```

FIGURE 4J

```
BH10  TTCTATGTAGATGGGCAGCTAACAGGGAGACTAAATTAGGAAAAGCAGGATATGTTACTAACAAAGGAAGACAA  3521
      PheTyrValAspGlyAlaAlaAsnArgGluThrLysLeuGlyLysAlaGlyTyrValThrAsnLysGlyArgGln
BH5   ---------------------------G-------------------------------------T-G------
                                 Ser                                      Arg

BH10  AAGGTTGTCCCCCTAACTAACACAACAAATCAGAAAACTGAGTTACAAGCAATTTATCTAGCTTTGCAGGATTCA  3596
      LysValValProLeuThrAsnThrThrAsnGlnLysThrGluLeuGlnLeuGlnAlaIleTyrLeuAlaLeuGlnAspSer
BH5   --A-----A-----------------------------------G-----A-----------------------G
                Thr                                                          Asn

BH10  GGATTAGAAGTAAACATAGTAACAGACTCACAATATGCATTAGGAATCATTCAAGCACAACCAGATAAAAGTGAA  3671
      GlyLeuGluValAsnIleValThrAspSerGlnTyrAlaLeuGlyIleIleGlnAlaGlnProAspLysSerGlu
BH5   -----------------T--------------------------------------------------------

BH10  TCAGAGTTAGTCAATCAAATAATAGAGCAGTTAATAAAAAGGAAAAGGTCTATCTGGCATGGGTACCAGCACAC  3746
      SerGluLeuValAsnGlnIleIleGluGlnLeuIleLysLysLysGluLysValTyrLeuAlaTrpValProAlaHis
BH5   ----------------------------------------------------------------------
                                                              Kpn I

BH10  AAAGGAATTGGAGGAAATGAACAGTAGATAAATTAGTCAGTGCTGAATCAGGAAAATACTATTTTTAGATGGA  3821
      LysGlyIleGlyGlyAsnGluGlnValAspLysLeuValSerAlaGlyIleLysArgLysIleLeuPheLeuAspGly
BH5   --------------------------------------------------------------------

BH10  ATAGATAAGGCCCAAGATGAACATGAGAAATATCACAGTAATTGGAGAGCAATGGCTAGTGATTTAACCTGCCA  3896
      IleAspLysAlaGlnAspGluHisGluLysTyrHisSerAsnTrpArgAlaMetAlaSerAspPheAsnLeuPro
BH5   -----------------------A----------------------------------------------
```

FIGURE 4K

```
                Pvu II
BH10  CCTGTAGTAGCAAAAGAAATAGTAGCCAGCTGTGATAAATGTCAGCTAAAGGAGAAGCCATGCATGACAAGTA    3971
      ProValAlaLysGluIleValAlaSerCysAspLysCysGlnLeuLysGlyGluAlaMetHisGlyGlnVal
BH5   ------------------------------------------------------------------------

BH10  GACTGTAGTCCAGGAATATGGCAACTAGATTGTACACATTTAGAAGGAAAAGTTATCCTGGTAGCAGTTCATGTA   4046
      AspCysSerProGlyIleTrpGlnLeuAspCysThrHisLeuGluGlyLysValIleLeuValAlaValHisVal
BH5   -------------------------------------------------------------------------

Aha III
BH10  GCCAGTGGATATATAGAAGCAGAAGTTATTCCAGCAGAAACAGGGCAGGAAACAGCATATTTCTTTTAAAATTA   4121
      AlaSerGlyTyrIleGluAlaGluValIleProAlaGluThrGlyGlnGluThrAlaTyrPheLeuLeuLysLeu
BH5   -------------------------------------------------------------------------

BH10  GCCAGTGGATATATAGAAGCAGAAGTTATTCCAGCAGAAACAGGGCAGGAAACAGCATATTTCCAGTGCTACGGTTAAGGCCCCC   4196
      AlaGlyArgTrpProValLysThrIleHisThrAspAsnGlySerAsnPheThrSerAlaThrValLysAlaAla
BH5   -------------------------------------------------------------------------

Eco RI
BH10  TGTTGGTGGGCGGAATCAAGCAGGAATTTGAATTCCCTACAATCCCCAAAGTCAAGGAGTAGTAGAATCTATG    4271
      CysTrpTrpAlaGlyIleLysGlnGluPheGluPheProTyrAsnProGlnSerGlnValValGluSerMet
BH5   -------------------------------------------------------------------------

BH10  AATAAAGAATTAAAGAAAATTATAGGACAGGTAAGAGATCAGGCTGAACATCTTAAGACAGCAGTACAAATGGCA   4346
      AsnLysGluLeuLysLysIleIleGlyGlnValArgAspGlnAlaGluHisLeuLysThrAlaValGlnMetAla
BH5   -------------------------------------------------------------------------
```

FIGURE 4L

```
              Aha III
BH10  GTATTCATCCACAATTTAAAGAAAGGGGGATTGGGGGTACAGTGCAGGGGAAAGAATAGTAGACATAATA  4421
      ValPheIleHisAsnPheLysArgLysGlyIleGlyLysGlyTyrSerAlaGlyGluArgIleValAspIleIle
BH5   ------------------------------------------------------------------------

BH10  GCAACAGACATACAAACTAAAGAATACAAAACAATTACAAAATTCAAAATTTCGGGTTTATTACAGGGAC  4496
      AlaThrAspIleGlnThrLysGluLeuGlnLysGlnIleThrLysIleAsnPheArgValTyrTyrArgAsp
BH5   ------------------------------------------------------------------------

BH10  AGCAGAAATCCACTTTGGAAGGACCAGCAAAGCTCCTCTGAAAGGTGAAGGGGCAGTAGTAATACAAGATAAT  4571
      SerArgAsnProLeuTrpLysGlyProAlaLysLeuLeuTrpLysGlyGluGlyAlaValValIleGlnAspAsn
BH5   ------------------------------------------------------------------------
                              --------SOR

BH10  AGTGACATAAAAGTAGTCCAAGAAGAAAAGCAAAGATCATTAGGGATTATGAAAACAGATGCCAGGTGATGAT  4646
      SerAspIleLysValValProArgArgLysAlaLysIleIleArgAspTyrGlyLysGlnMetAlaGlyAspAsp
      CysGlnGluGluLysGlnArgSerLeuGlyIleMetGluAsnArgTrpGlnValMetIle
BH5   ------------------------------------------------------------------------
              -----POL-----
BH10  TGTGTGGCAAGTAGACAGGATGAGGATTAGAACATGGAAAAGTTAGTAAAACACCATATGTATGTTTCAGGAA  4721
      CysValAlaSerArgArgMetArgIleArgThrTrpLysSerLeuValLysHisHisMetTyrValSerGlyLys
      ValTrpGlnValAspArgMetArgIleArgThrTrpLysSerLeuValLysHisHisMetTyrValSerGlyLys
BH5   ---------------------------------G--------------------------------------
                                        Arg
```

FIGURE 4M

```
BH10  AGCTAGGGGATGGTTTTATAGACATCACTATGAAAGCCCTCATCCAAGAATAAGTTCAGAAGTACACATCCCACT    4796
      AlaArgGlyTrpPheTyrArgHisHisTyrGluSerProArgIleSerSerGluValHisIleProLeu
BH5   ------------------------------------------------------------------------

BH10  AGGGGATGCTAGATTGGTAATAACAACATATTGGGGTCTGCATACAGGAGAAAGAGACTGGCATTGGGTCAGGG    4871
      GlyAspAlaArgLeuValIleThrThrTyrTrpGlyLeuHisThrGlyGluArgAspTrpHisLeuGlyGlnGly
BH5   ------------------------------------------------------------------------

BH10  AGTCTCCATAGAATGGAGGAAAAGAGATATAGCACACAAGTAGACCCTGAACTAGCAGACCAACTAATTCATCT    4946
      ValSerIleGluTrpArgLysLysArgTyrSerThrGlnValAspProGluLeuAlaAspGlnLeuIleHisLeu
BH5   -------------G----------------------------------------------------------
                   Arg

BH10  GTATTACTTTGACTGTTTTTCAGACTCTGCTATAAAAGGCCTTATTAGGACACATAGTTAGCCCTAGGTGTGA    5021
      TyrTyrPheAspCysPheSerAspSerAlaIleArgLysAlaLeuLeuGlyHisIleValSerProArgCysGlu
BH5   -C------T---------------------------------------------------------------

BH10  ATATCAAGCAGGACATAACAAGTAGGATCTCTACAATACTTGGCACTAGCAGCATTAATAACACCAAAAAAGAT    5096
      TyrGlnAlaGlyHisAsnLysValGlySerLeuGlnTyrLeuAlaLeuAlaAlaLeuIleThrProLysLysIle
BH5   -------------------------------------------------------------G----------
                                                                    Val

BH10  AAAGCCACCTTTGCCTAGTGTTACGAAACTGACAGAGGATAGATGGAACAGCCCCAGAAGACCAAGGGCCACAG    5171
      LysProProLeuProSerValThrLysLeuThrGluAspArgTrpAsnSerProGlnLysThrLysGlyHisArg
BH5   ------------------------------------------------------------------------
```

FIGURE 4N

```
BH10   SOR--------
       AGGGAGCCACACAATGAATGAGACACTAGAGCTTTTAGAGGAGCTTAAGAATGAAGCTGTTAGACATTTCCTAGG    5246
       GlySerHisThrMetAsnGlyHis
BH5    ---A--------------------------------------------------------------------

BH10   ATTTGGCTCCATGGCTTAGGGCAACATATCTATGAAACTTATGGGGATATACTTGGGCAGGAGTGGAAGCCATAATA    5321
BH5    --------------------------------------------------------------------------

Sal I
BH10   AGAATTCTGCAACAACTGCTGTTTATCCATTTTCAGAATTGGGTGTGTCGACATAGCAGAATAGGCGTTACTCGACA    5396
       Eco RI
BH5    -------------------------------------------------------------A-----------

BH10   GAGGAGAAGAATGGAGCCAGTAGATCCTAGACTAGAGCCCTGGAAGCATCCAGGAAGTCAGCCTAAAACTG    5471
BH5    --------------------------------------------------------------------

BH10   CTTGTACCAATTGCTATTGTAAAAGTGTTGCTTTCATTGCCAAGTTTGTTTCATAACAAAGCCTTAGGCATCT    5546
BH5    -------------C---------------------------------------------------------

(Sst I)
BH10   CCTATGGCAGGAAGAAGCGGAGACAGGCGACGAAGAGCTCCTCAAGGCCAGTCAGACTCATCAAGTTTCTCTATCAA    5621
BH5    -------------------------------------G---
BH8    -----------------G---A--G-A-----------------------------------------

BH10   AGCAGTAAGTAGTACATGTAATGCAACCTATACAAATAGCAATAGTAGCA( )TTAGTAGTAGCAATAATATAGCAA    5696
BH8    ---------------------------C-----C-----T-C-A---T-GCC----C-----------
```

FIGURE 40

```
BH10  TAGTTGTGTGGTCCATAGTAATCATAGAATATTAAGACAAAGAAAAATAGACAGGTTAATTGATA    5771
BH8   ----------------------------------------------------------------

BH10  GACTAATAGAAAGAGACAGAACAGTGGCAATGAGAGTGAAGGAGAAATATCAGCACTTGTGGAGATGGGGGTGG  5846
          -----ENV-LOR
            LysGluGlnLysThrValAlaMetArgValLysGluLysTyrGlnHisLeuTrpArgTrpGlyTrp
BH8   ---------------------------------------------------------------------------

BH10  AGATGGGGCACCATGCTCCTTGGATGTTGATGATCTGTAGTGCTACAGAAAAATTGTGGGTCACAGTCTATTAT  5921
      ArgTrpGlyThrMetLeuLeuGlyMetIleCysSerAlaThrGluLysLeuTrpValThrValTyrTyr
BH8   ----------------------------------------------T------------------T--
                                                                          Phe

Kpn I
BH10  GGGGTACCTGTGTGAAGGAAGCAACCACCACTCTATTTTGTGCATCAGATGCTAAAGCATATGATACAGAGTA  5996
      GlyValProValTrpLysGluAlaThrThrThrLeuPheCysAlaSerAspAlaLysTyrAspThrGluVal
BH8   -------------------------------------------------------------------------

BH10  CATAAATGTTTGGGCCACACATGCCTGTGTACCCACAGACCCCAACCCACAAGAAGTAGTAGTATTGGTAAATGTGACA  6071
      HisAsnValTrpAlaThrHisAlaCysValProThrAspProAsnProGlnGluValValLeuValAsnValThr
BH8   ------------------------------------*---------------------------------------

BH10  GAAAATTTAACATGTGGAAAAATGACATGTAGAACAGATGCATGAGGATATAATCAGTTTATGGGATCAAAGC  6146
      GluAsnPheAsnMetTrpLysAsnAspMetValGluGlnMetHisGluAspIleIleSerLeuTrpAspGlnSer
BH8   ---------------------------------------------------------------------------
```

FIGURE 4P

```
                  Aha III
BH10  CTAAAGCCATGTGTAAAATTAACCCCACTCTGTGTTAGTTTAAGTGCACTGATTTGAAGAATGATACTAATACC  6221
      LeuLysProCysValLysLeuThrProLeuCysValSerLeuLysThrAspLeuLysCysThrAsnThrAsnThr
BH8   ----------------------------------------------------------------------------

BH10  AATAGTAGTAGCGGGAGAATGATAATGGAGAAAGGAGAGATAAAAACTGCTCTTCAATATCAGCACAAGCATA    6296
      AsnSerSerGlyArgMetIleMetGluLysGlyGluIleLysAsnCysSerPheAsnIleSerThrSerIle
BH8   --------------------------------------------------------------------A---
                                                                           Lys

BH10  AGAGGTAAGGTGCAGAAAGAATATGCATTTTTTATAAACTGATATAATACCAATAGATAATGATACTACCAGC  6371
      ArgGlyLysValGlnLysGluTyrAlaPhePheTyrLysLeuAspIleIleProIleAspAsnAspThrThrSer
BH8   ----------------------------------------------------------------------------

BH10  TATACGTTGACAAGTTGTAACACCTCAGTCATTACACAGGCCTGTCCAAAGGTATCCTTTGAGCCAATTCCATA  6446
      TyrThrLeuThrSerCysAsnThrSerValIleThrGlnAlaCysProLysValSerPheGluProIleProIle
BH8   ----------------------------------------------------------------------------

BH10  CATTATTGTGCCCCGGCTGGTTTTTGCAGATTCTAAAATGTAATAATAATAGAGCGTTCAATGAACAGAGACCATGTACA  6521
      HisTyrCysAlaProAlaGlyPheAlaIleLeuLysCysAsnAsnLysThrGlyPheAsnGlyThrGlyProCysThr
BH8   ----------------------------------------------------------------------------

BH10  AATGTCAGCACAGTACAATGTACACATGAATTAGGCCAGTAGTATCAACTCAACTGCTGTTAAATGGCAGTCTG  6596
      AsnValSerThrValGlnCysThrHisGlyIleArgProValValSerThrGlnLeuLeuAsnGlySerLeu
BH8   ----------------------------------------------------------------------------
```

FIGURE 4Q

```
                           BglII ■                                    PvuII ■
BH10  GCAGAGAAGAGGTAGTAATTAGATCTGCCAATTTCACAGACAATGCTAAAACCATAATAGTACAGCTGAACCAA    6671
      AlaGluGluGluValIleArgSerAlaAsnPheThrAspAsnAlaLysThrIleIleValGlnLeuAsnGln
BH8   ----------------------------T-----G----------------------------G--AC-
                                  Val                                   AspThr

BH10  TCTGTAGAAATTAATTGTACAAGACCCAACAACAATACAAGAAAAAGTATCCGTATCCAGAGAGGACCAGGAGA    6746
      SerValGluIleAsnCysThrArgProAsnAsnAsnThrArgLysSerIleArgIleArgGlyProGlyArg
BH8   ----------------------------------------------AA-------------G--------
                                                    Lys

BH10  GCATTTGTTACAATAGGAAAAATATGAGACAAGCACACATTGTAACATTAGTAGAGCAAAATGGAATAAC       6821
      AlaPheValThrIleGlyLysIleGlyAsnMetArgGlnAlaHisCysAsnIleSerArgAlaLysTrpAsnAsn
BH8   -----------------------------------------------------------GC-
                                                                 Ala

AhaIII ■
BH10  ACTTTAAAACAGATAGCAAATTAAGAGAACAATTTGGAAATAAACAATAATCTTTAAGCAGTCCTCA          6896
      ThrLeuLysGlnIleAspSerLysLeuArgGluGlnPheGlyAsnAsnLysThrIleIlePheLysPheSer
BH8   ----------------------------------------------------------------

BH10  GGAGGGGACCCAGAAATTGTAACGCACACAGTTTAATTGTGGAGGGGAATTTTCTACTGTAATTCAACACACTG   6971
      GlyGlyAspProGluIleValThrHisSerPheAsnCysGlyGlyGluPhePheTyrCysAsnSerThrGlnLeu
BH8   -----------------------------------------------------------------
```

FIGURE 4R

```
BH10   TTTAATAGTACTTGGTTTAATAGTACTTGGAGTACTAAAGGTCAAATAACACTGAAGGAAGTGACACAATCACC   7046
       PheAsnSerThrTrpPheAsnSerThrTrpSerThrLysGlySerAsnThrGluGlySerAspThrIleThr
BH8    ----------------------------(

BH10   CTCCCATGCAGAATAAACAAATTATAAACATGTGCAGGAAGTAGAAAAGCAATTGTATGCCCCTCCATCAGT   7121
       LeuProCysArgIleLysGlnIleIleLysAsnMetTrpGlnGluValGlyLysAlaMetTyrAlaProProIleSer
BH8

BH10   GGACAAATTAGATGTGTTCATCAAATATTACAAGGGCTGCTATTAACAAGAGATGTGGTAATAGCAACAATGAGTCC   7196
       GlyGlnIleArgCysSerSerAsnIleThrGlyLeuLeuLeuThrArgAspGlyGlyAsnSerAsnGluSer
BH8                                                             ■

BolII
BH10   GAGATCTTCAGACCTGGAGGAGGAGATATGAGGGACAATTGGAGAGAAGTGAATTATATAAATATAAAGTAGTAAAA   7271
       GluIlePheArgProGlyGlyGlyAspMetArgAspAsnTrpArgSerGluLeuTyrLysTyrLysValValLys
BH8

BH10   ATTGAACCATTAGGAGTAGCACCCACCAAGGCAAAGAGAAGAGTGGTGCAGAGAGAAAAAAGAGCAGTGGAATA   7346
       IleGluProLeuGlyValAlaProThrLysAlaLysArgArgValValGlnArgGluLysArgAlaValGlyIle
BH8

BH10   GGAGCTTTGTTCCTTGGGTTCTTGGGAGCAGCAGGAAGCACTATGGGCGCAGCGTCAATGACGCTGACGGTACAG   7421
       GlyAlaLeuPheLeuGlyPheLeuGlyAlaAlaGlySerThrMetGlyAlaAlaSerMetThrLeuThrValGln
BH8
```

FIGURE 4S

```
BH10  GCCAGACAATTATTGTCTGGTATAGTGCAGCAGCAGAACAATTGCTGAGGGCTATTGAGGCGCAACACAGATCTG    7496
      AlaArgGlnLeuLeuSerGlyIleValGlnGlnGlnAsnAsnLeuLeuArgAlaIleGluAlaGlnGlnHisLeu
BH8   ------------------------------------------------------------GC--------------
                                                                  Gly

BH10  TTGCAACTCACAGTCTGGGCATCAAGCAGCTCCAGGCAAGAATCCTGGCTGTGAAAGATACCTAAGGATCAA      7571
      LeuGlnLeuThrValTrpGlyIleLysGlnLeuGlnAlaArgIleLeuAlaValGluArgTyrLeuLysAspGln
BH8   ----------------------------------------------------------------------------

BH10  CAGCTCCTGGGGATTTGGGGTTGCTCTGGAAAACTCATTTGCCACCACTGCTGTGCCTTGGAATGCTAGTTGGAGT  7646
      GlnLeuLeuGlyIleTrpGlyCysSerGlyLysLeuIleCysThrThrAlaValProTrpAsnAlaSerTrpSer
BH8   ----------------------------------------------------------------------------
                                                                        ■    Hind III
BH10  AATAAATCTCTGGAACAGATTTGGAATAACATGACCTGATGAGTGGGACAGAGAAATTAACAATTACACAAGC    7721
      AsnLysSerLeuGluGlnIleTrpAsnAsnMetThrTrpMetGluTrpAspArgGluIleAsnAsnTyrThrSer
BH8   ■---------------------------------------------------------------------------

BH10  TTAATACACTCCTTAATTGAAGAATCGCAAAACCAGCAAGAAAAGAATGAACAAGAATTATTGGAATTAGATAAA    7796
      LeuIleHisSerLeuIleGluGluSerGlnAsnGlnGlnGluLysAsnGluGlnGluLeuLeuGluLeuAspLys
BH8   ----------------------------------------------------------------------------

BH10  TGGGCAAGTTTGTGGAATTGGTTTAACATAACAAATTGGCTGTGGTATATAAAATTATTCATAATGATAGTAGGA    7871
      TrpAlaSerLeuTrpAsnTrpPheAsnIleThrAsnTrpLeuTrpTyrIleLysLeuPheIleMetIleValGly
BH8   ------------■---------------------------------------------------------------
```

FIGURE 4T

```
BH10  GGCTTGGTAGGTTTAAGAATAGTTTTTGCTGTACTTTCTGTAGTGAATAGAGTTAGGCAGGATATATTCACCATTA    7946
      GlyLeuValGlyLeuArgIleValPheAlaValLeuSerValValAlaAsnArgValAlaArgGlnGlyTyrSerProLeu
BH8   -------------------------------------A--------------------------------------
                                            Ile

BH10  TCGTTTCAGACCCACCTCCCAATCCCGAGGGACCCGACAGGCCCGAAGGAATAGAAGAAGGTGGAGAGAGA        8021
      SerPheGlnThrHisLeuProIleProGluGlyProAspArgProGluGlyIleGluGluGluGlyGlyGluArg
BH8   -------------------------------------A--------------------------------------
                                            Asn

Bam HI
BH10  GACAGAGACAGATCCATTCGATTAGTGAACGGATCCTTAGCACTTATCTGGGACGATCTCGCGAGCCTGTGCCTC    8096
      AspArgAspArgSerIleArgLeuValAsnGlySerLeuAlaLeuIleTrpAspAspLeuArgSerLeuCysLeu
BH8   ---------------------------------------------------------------------------

BH10  TTCAGCTACCACCGCTTGAGAGAGACTTACTCTTGATTGTAACGAGGATTGTGGAACTTCTGGGACGCAGGGGTGG  8171
      PheSerTyrHisArgLeuArgAspLeuLeuLeuIleValThrArgIleValGluLeuLeuGlyArgArgGlyTyrTrp
BH8   ---------------------------------------------------------------------------

(Mpe I)
BH10  GAAGCCCTCAAATATTGGTGGAATCCTCCTACAGTATTGGAGTCAGAGCTAAAGAATAGTGCTGTTAGCTTGCTC    8246
      GluAlaLeuLysTyrTrpTrpAsnLeuLeuGlnTyrTrpSerGlnGluLeuLysAsnSerAlaValSerLeuLeu
BH8   -------------------------------------A--------------------------------------
                                            Asn
```

FIGURE 4U

```
BH10   ■AATGCCACAGCTATAGCAGTAGCTGAGGGGACAGATAGGGTTATAGAAGTAGTACAAGGAGCTTATAGAGCTATT   8321
        AsnAlaThrAlaIleAlaValAlaGluGlyThrAspArgValIleGluValValGlnGlyAlaTyrArgAlaIle
BH8    ----------------------------------------T--------C---------------------C----
                                                 Leu     Ala
                  ENV-LOR-------

BH10   CGCCACATACCTAGAAGAATAAGACAGGGCTTGGAAAGGATTTGCTATAAGATGGTGGCAAGTGGTCAAAAAG    8396
        ArgHisIleProArgArgIleArgGlnGlyLeuGluArgIleLeuLeu
BH8    ----------------------------------------------------------------------------

BH10   TAGTGTGGTTGGATGGCCTGCTGTAAGGGAAAGAATGAGACAGCTGAGCCAGCAGATGGGGTGGGAGCAGC     8471
BH8    ------------------------------------------------------------------------T---

Xho I
BH10   ATCTCGAGACCTAGAAAAACATGGAGCAATCACAAGTAGCAACACAGCAGCTAACAATGCTGATTGTGCCTGGCT   8546
BH8    -------------------------------------------T----------------C-----------T---

Kpn I
BH10   AGAAGCACAAGAGGAGGAGGAGGTGGGTTTTCCAGTCACACCTCAGTTACCTTTAAGACCAATGACTTACAAGGC   8621
BH5    -----------------------------------------Aha III--------US
       PvuII Bgl II

Polymurine Track IR
BH10   AGCTGTAGATCTTAGCCACTTTTAAAAGAAAAGGGGGACTGGAAGGGCTAATTCACTCCCAACGAAGACAAGA    8696
BH8    ----------------------------------------------------------------------------
```

FIGURE 4V

```
           (Bam HI)
BH10  TATCCTGTGATCTGTGTGGATCTACCACACACAAGGCTACTTCCCTGATTAGCAGAACTACACACCAGGGCCAGGAT    8771
BH8   ------------------------C----------------------------------------------AG--

BH10  CAGATATCCACTGACCTTTGGATGGTGCTACAAGCTAGTACCAGTTGAGCCAGAGAAGTTAGAAGAAGCCAACAA    8846
BH8   ------------G--------------------------------A---------------T--

BH10  AGGAGAGAACACCAGCTTGTTACACCCTGTGAGCCTGCATGGAATGGATGACCCGGAGAGAGAAGTGTTAGAGTG    8921
BH8   -----------------------------------T--

BH10  GAGGTTTGACACCCGCCTAGCATTTCATCACATGGCCCGAGAGCTGCATCCGGAGTACTTCAAGAACTGCTGACA    8996
BH8   ----------------------------------------------------T--

BH10  TCGAGCTTGCTACAAGGGACTTTCCGCTGGGGACTTTCCAGGGAGGCGTGGCCTGGGCGGGACTGGGGAGTGGCG    9071
BH8

Pvu II              US----R      Bal II
BH10  AGCCCTCAGATCCTGCATATAAGCAGCTGCTTTTTGCCTGTACTGGGTCTCTCTGGTTAGACCAGATCTGAGCCT    9146
BH8   --Sst I----
```

FIGURE 4W

```
              R
BH10    GGGAGCTC
BH8     --------

Hink III
                    Poly(A) site              R------                          9154
MXB2    TCTGGCTAGCTAGGGAACCCACTGCTTAAGCCTCAATAAAGCTTGCCTTGAGTGCTTCA
                                     ----US
MXB2                                 AGTAGTGTGCCCGTCTGTTGTGTGACTCTGGTAACTAGAGATCCCTCAGA    9213
                                     us-----
                                       IR
MXB2    CCCTTTTAGTCAGTGTCAGTGTGGAAAATCTCTAGCA
```

EXPRESSION OF HUMAN IMMUNODEFICIENCY VIRUS (HIV) REVERSE TRANSCRIPTASE

This invention was made with government support under Grant Number CA 30488 from the National Cancer Institute of the United States Department of Health and Human Services. The U.S. government has certain rights in this invention.

This is a continuation of application Ser. No. 552,848 filed Jul. 12, 1990, now abandoned, which is a continuation of Ser. No. 865,156, filed May 20, 1986, now abandoned.

BACKGROUND OF THE INVENTION

Within this application several publications are referenced by number within parentheses. Full citations for these publications may be found at the end of the specification immediately preceding the claims. The disclosures of these publications in their entireties are hereby incorporated by reference into this application in order to more fully describe the state of the art to which the invention pertains.

Acquired Immune Deficiency Syndrome (AIDS) is a new epidemic characterized by a marked depletion of the cellular immune response. The causative agent of the disease is now firmly established to be the human retrovirus known as Human Immunodeficiency Virus Type 1 (HIV-1), but was formerly known as Human T-cell lymphotropic virus III or Lymphadenopathy virus (HTLV-III/LAV) (1-4). Efforts to arrest the spread of this virus are being made on two broad fronts: the development of antiviral vaccines which might allow immunized individuals to resist infection, and the development of antiviral drugs which would specifically retard or arrest viral replication. One potentially important target of such drugs is the virion-associated enzyme reverse transcriptase (5-8).

In the early stages of the retroviral life cycle, viral RNA is copied to form a double-stranded DNA, which is integrated into host DNA to generate the provirus (for review, 1). The synthesis of the proviral DNA is catalyzed by the enzyme reverse transcriptase, which may efficiently utilize either RNA or DNA templates for DNA synthesis by the elongation of a primer bearing a paired 3' hydroxyl terminus. Inherent in the same protein is a second activity, RNAse H, which degrades RNA present as a duplex RNA:DNA hybrid. The viral pol gene encodes many enzymatic activities which participate in various steps of the life cycle. The pol gene product is initially expressed as a polyprotein Pr200gag-pol (2,3), containing sequences encoded by the gag gene fused to sequences encoded by the pol gene; proteolytic processing is required to remove the sequences and to excise the mature products from the pol sequences.

Reverse transcriptase is widely used as a means of producing complementary DNA (cDNA) copies of messenger RNA (mRNA) molecules. These cDNAs may be inserted into expression vectors which are used to transform cells so that the resulting cells produce a desired polypeptide encoded by the original mRNA.

The HTLV-III reverse transcriptase has been purified in small quantities and some of its properties are established. The enzyme has unusual template and divalent cation preferences (9-11), suggesting that specific inhibitors of the enzyme may be discovered. Certain inhibitors of HTLV-III reverse transcriptase activity may be used to block the activity of this enzyme as it is produced by viruses infecting human cells and tissues.

Reverse transcriptase being an integral part of the viral life cycle, this will allow use of the inhibitors to treat or prevent HTLV-III related diseases. The isolation of such inhibitors would be facilitated by the availability of larger quantities of the active enzyme.

Reverse transcriptase produced by and isolated from virions is commercially available. However, it is quite expensive due to the low abundance of the gene product in the virions.

Several disclosures in the art concern the production of a polypeptide having reverse transcriptase activity by bacteria transformed with genetically engineered vectors. One disclosure involves the shotgun cloning into *Escherichia coli* of total genomic DNA isolated from the cells of warm-blooded vertebrate animals, e.g. fowl liver cells, [Japanese patent publication no. 56087600].

Two other disclosures detail the expression of a segment of the retrovirus pol gene to produce reverse transcriptase in *E. coli* in high yield (16, 17).

Co-pending, co-assigned U.S. patent application Ser. No. 731,128, filed May 6, 1985 describes the expression of enzymatically active reverse transcriptase from Moloney murine leukemia virus (MuLV) in relatively high yield.

The present invention uses a modified region of the HTLV-III pol gene which is inserted into a plasmid, its transcription being controlled by an inducible promoter. The expression of the inserted gene fragment results in the production of a polypeptide with HTLV-III reverse transcriptase activity.

Additionally, the present invention describes a method for identifying substances which inhibit HTLV-III reverse transcriptase activity.

SUMMARY OF THE INVENTION

The invention concerns a double-stranded DNA plasmid which, when expressed in a suitable host cell, produces a polypeptide having HTLV-III reverse transcriptase activity, the plasmid comprising in 5' to 3' order:

- a DNA sequence which includes an inducible promoter;
- a DNA sequence which includes an ATG initiation codon;
- substantially all of the human T-cell lymphotropic virus (HTLV-III) pol gene, said gene including a DNA sequence which encodes the polypeptide having reverse transcriptase activity;
- a DNA sequence which contains a gene associated with a selectable or identifiable phenotypic trait which is manifested when the vector is present in the host cells; an
- a DNA sequence which contains an origin of replication from a bacterial plasmid capable of autonomous replication in the host cell.

The plasmid of this invention may be introduced into a suitable host cell where the gene may be expressed under suitable conditions. In a presently preferred embodiment, the plasmid is pHRT25 and the host cell is an *Escherichia coli* HB101 cell (deposited together under ATCC No. 67117. Suitable inducible promoters are ones which are induced when the host cell is grown in a medium deficient in one or more amino acids. One such inducible promoter is in the Trp operon of *E. coli*.

The invention also concerns a method for identifying substances which inhibit HTLV-III reverse transcriptase. The method comprises isolating HTLV-III reverse transcriptase, contacting the reverse transcriptase so isolated with an RNA molecule to be reverse transcribed in the presence of a suitable amount of a mixture of deoxyribonucleotides to produce a transcription cocktail, contacting the transcription cocktail with an amount of a substance to be identified for a suitable period and detecting the amount of reverse transcriptase activity in the cocktail, a significant decrease in the amount of reverse transcriptase activity relative to the amount of activity in a cocktail not contacted with the substance indicating an inhibition of the reverse transcriptase activity.

Finally, the invention comprises a method for treating an HTLV-III virus-related disease. The method comprises administering to the patient a suitable amount of a physiologically acceptable HTLV-III reverse transcriptase inhibiting substance for a suitable period.

A 3.7 kb fragment of cloned proviral HTLV-III DNA was excised by cleavage with Bgl II plus Sal I and inserted into the expression plasmid at the BamHI and Sal I sites. Cloning procedures were as described previously (16–18). Parallel constructions were performed to insert the same pol sequences into the pATH3 vector in the wrong reading frame to form the plasmids pHRT31 and pHRT32.

Figure 2:
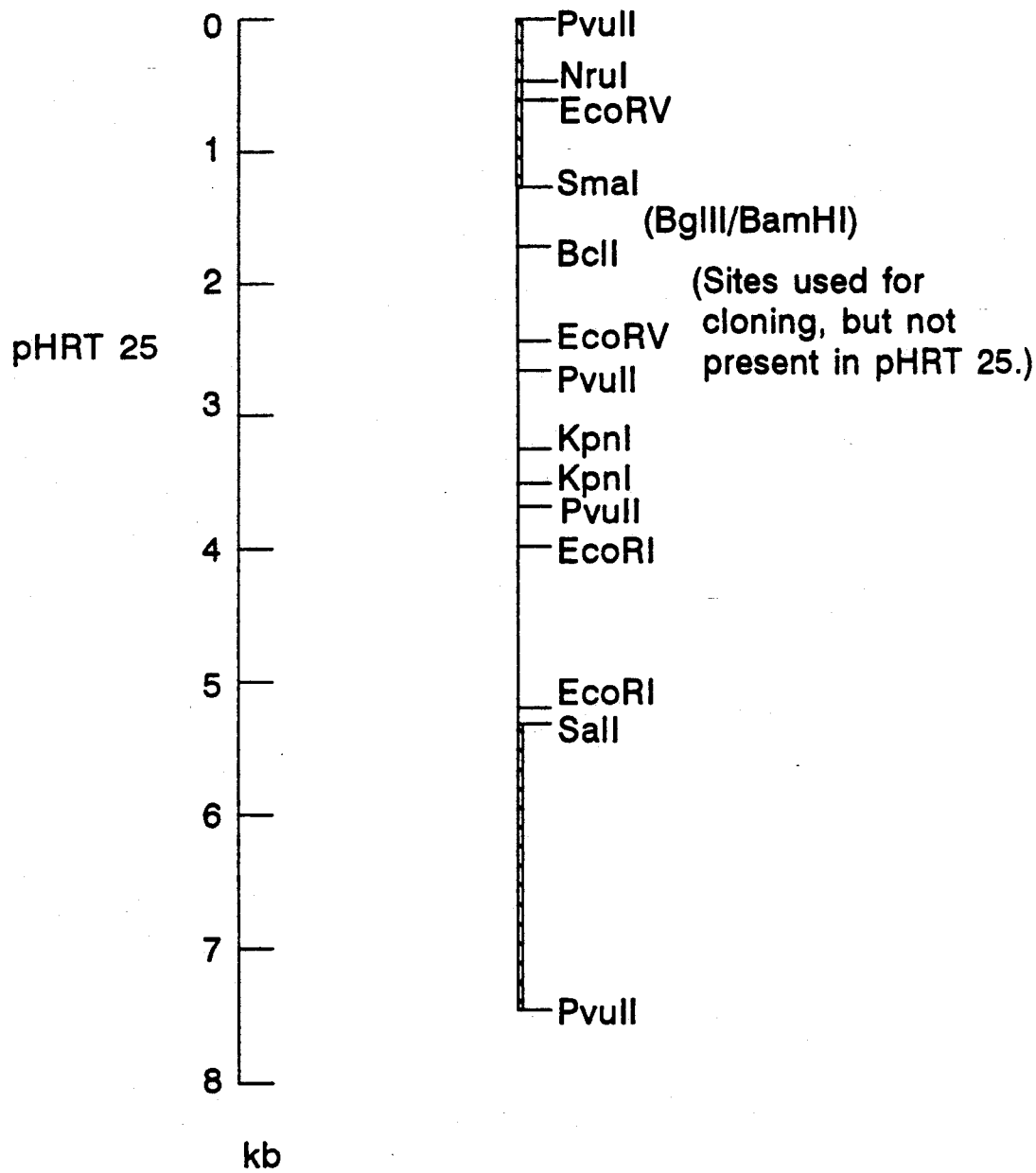

FIG. 2. Restriction map of clone pHRT5 containing pol region of HTLV-III.

This map shows restriction sites in the vector (pATH2, dark lines) and in the insert (pol region of HTLV-III, light lines). Start of insert is at about nucleotide 1640 (BglII site of HTLV-III) and end of insert is at about nucleotide 5368 (SalI site in HTLV-III) from HTLV-III map of Ratner, et al. (12) (see FIG. 4).

Figure 3A:
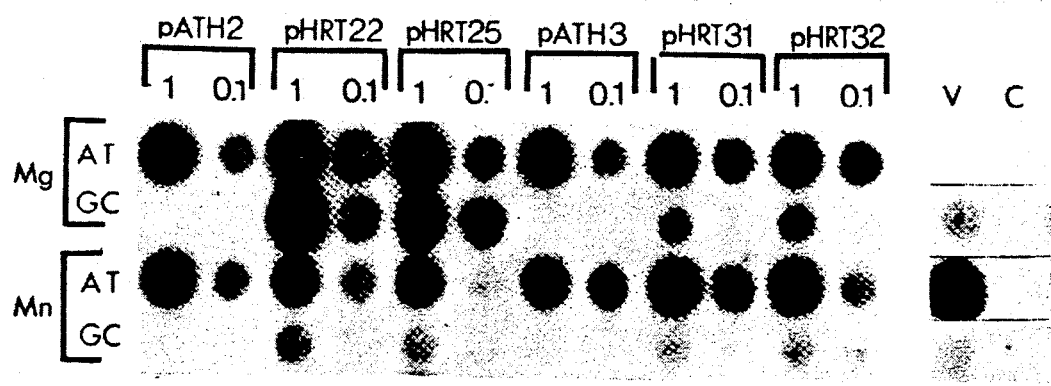
Figure 3B:
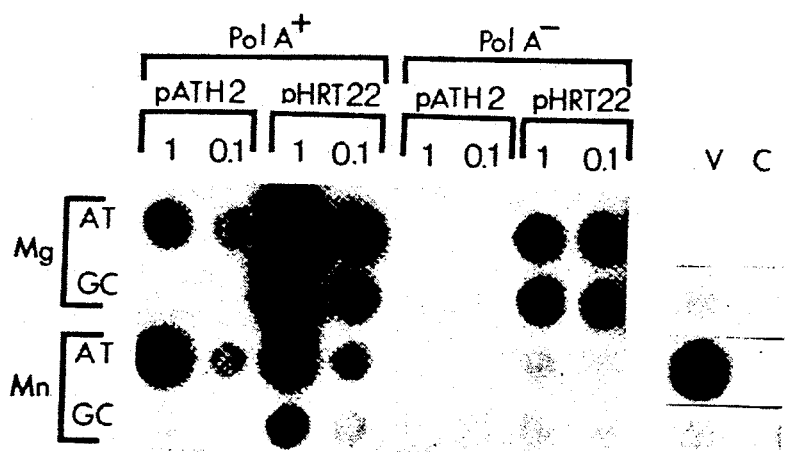

FIG. 3A-B. Reverse transcriptase assays of crude bacteria extracts.

Cultures were grown, starved for tryptophan, and lysed as described previously (14-17). Panel A: HB101 cells carrying the indicated plasmids were used. Either 1 ul or 0.1 ul of each extract as indicated was incubated in 50 ul reaction cocktails containing 50 mM Tris-HCl pH 8.3, 30 mM DTT, 60 mM NaCl, 0.05% NP40, and 10 uM of the appropriate a-$^{32}$P deoxyribonucleotide (1 Ci/mmole). Reactions contained either Mg++ (10 mM) or Mn++ (1 mM) as indicated at the left. Rows marked AT included substrates poly(rA) (10 ug/ml) and oligo(dT) (5 ug/ml), while rows marked GC included substrates poly(rC) (10ug/ml) and oligo(dG) (5 ug/ml; all homopolymers from Collaborative Research). Reactions were allowed to proceed for 30 min, and terminated by spotting 10 ul on DEAE paper (DE81; Whatman). The paper was washed at room temperature in 2XSSC (0.3 M NaCl, 0.03 M Sodium Citrate) for 3×10 min each, rinsed twice with 95% Ethanol, dried, and exposed to X-ray film. Samples marked V and C are assays of authentic reverse transcriptase from Moloney murine leukemia virus, and of medium from control cells. Panel B: HB101 (PolA+) and C2110 (PolAl−) cells carrying the indicated plasmids were used. Assays and substrates were as in Panel A.

FIG. 4A-W. Sequence of the HTLV-III Gene.

This figure shows the nucleotide sequence of the HTLV-III gene as disclosed by Ratner, et al. (12).

DETAILED DESCRIPTION OF THE INVENTION

A double-stranded DNA plasmid has been made which, when expressed in a suitable host cell, produces a polypeptide having HTLV-III reverse transcriptase activity. The plasmid includes in 5' to 3' order: a DNA sequence which includes an inducible promoter; a DNA sequence which includes an ATG initiation codon; a portion of the Human T-cell lymphotropic virus III (HTLV-III) pol gene, said portion including a DNA sequence which encodes the polypeptide having HTLV-III reverse transcriptase activity; a DNA sequence which contains a gene associated with a selectable or identifiable phenotypic trait such as drug resistance, e.g. ampicillin resistance, which is manifested when the vector is present in the host cell; a DNA sequence which contains an origin of replication from a bacterial plasmid capable of autonomous replication in the host cell, e.g., *Escherichia coli*. In one embodiment the inducible promoter of the plasmid is one which is induced when the host cell is grown upon a medium deficient in one or more amino acids. Thus, the inducible promoter may be the Trp promoter *Escherichia coli* and the medium deficient in the amino acid tryptophan. In another embodiment the inducible promoter is one which is induced when the host cell is subjected to increased temperature.

The ATG initiation codon of the plasmid may be derived from the coding sequence of the Trp E protein of *Escherichia coli*, e.g. a DNA sequence derived from about a 1000 nucleotide long sequence encoding a portion of the Trp E protein of *Escherichia coli*. In one embodiment the origin of replication is derived from pBR322.

The plasmid may comprise a circular double-stranded DNA sequence such as the plasmid identified as pHRT25, having the restriction map shown in FIG. 2 and deposited in *E. coli* HB101 under ATCC No. 67117. The *E. coli* HB101 strain containing plasmid pHRT25 has been deposited with the American Type Culture Collection (ATCC), 12301 Parklawn Drive, Rockville, Md. 20852under ATCC Accession No. 67117 on May 20, 1986.

The portion of the HTLV-III pol gene of the plasmid may comprise the nucleotide sequence from about nucleotide 1640 to about nucleotide 5368(see FIG. 4). In one embodiment the 5' end of the central portion of the pol gene is 21 nucleotides from the start of the DNA sequence which encodes the polypeptide having reverse transcriptase activity.

Methods used in preparing the DNA vector and transforming suitable cells to the production of the polypeptide having reverse transcriptase activity are known in the art and described more fully hereinafter under Experimental Details.

Conventional cloning vehicles such as plasmids, e.g., pBR322, can be modified or engineered using known methods so as to produce novel cloning vehicles which contain DNA encoding a non-naturally occurring polypeptide having reverse transcriptase activity. Similarly, such cloning vehicles can be modified or engineered so that they contain DNA sequences, i.e., inducible promoters (Trp promoter, etc.), involved in the regulation or expression of the sequences encoding a polypeptide having reverse transcriptase activity. The DNA molecules so inserted may be made by various methods including enzymatic or chemical synthesis.

The resulting cloning vehicles are chemical entities which do not occur in nature and may only be created by the modern technology commonly described as recombinant DNA technology. These cloning vehicles, including the plasmid of this invention, may be introduced into a suitable host cell, either procaryotic, e.g., bacterial (*E. coli* or *B. subtilis*, etc.) or eucaryotic, e.g., yeast, using techniques known to those skilled in the art, such as transformation, transfection and the like. The one embodiment of this invention is the *E. coli* HB101 strain containing the plasmid pHRT25 deposited under ATCC No. 67117. The cells into which the plasmid of this invention is introduced will thus contain DNA encoding a non-naturally occurring polypeptide having reverse transcriptase activity. Further, the expression of the DNA encoding the non-naturally occurring polypeptide will be under the control of the Trp promoter.

The resulting cells into which DNA encoding the non-naturally occurring polypeptide encoding reverse transcriptase activity and encoding the Trp promoter has been introduced may be grown under suitable conditions known to those skilled in the art so as to control and effect the expression of the genetic information encoded by the DNA and permitting the production of the polypeptide having reverse transcriptase activity and the recovery of the resulting polypeptide. Thus one embodiment of this invention concerns the polypeptide so prepared, e.g. the polypeptide having reverse transcriptase activity characterized by being encoded by the plasmid pHRT25.

Another embodiment of this invention is a method for identifying substances which inhibit HTLV-III reverse transcriptase. The method comprises isolating HTLV-III reverse transcriptase, contacting the reverse transcriptase so isolated with an RNA molecule to be reversed transcribed in the presence of a suitable amount of a mixture of deoxyribonucleotides to produce a transcription cocktail, contacting the transcription cocktail with an amount of a substance to be identified for a suitable period and detecting the amount of reverse transcriptase activity in the cocktail, a significant decrease in the amount of reverse transcriptase activity relative to the amount of activity in a cocktail not contacted with the substance indicating an inhibition of the reverse transcriptase activity.

In the preferred embodiment, HTLV-III reverse transcriptase will be isolated from cells, i.e. bacterial or yeast cells containing plasmids comprising the HLTV-III pol gene, i.e. plasmid pHRT22 or pHRT25. HLTV-III reverse transcriptase may also be isolated from other sources, i.e., tissue culture cells infected with the HTLV-III virus. Methods used in isolating HTLV-III reverse transcriptase are known in the art and are described more fully hereinafter under Experimental Details.

Mixtures of deoxyribonucleotides to be used in the present invention will contain dATP, dGTP, dCTP and dTTP in relative amounts suitable t each experiment.

In the preferred embodiment, detecting the amount of reverse transcriptase activity comprises detecting by autoradiography the amount of one or more radiolabelled deoxyribonucleotides, i.e. $^{32}$P-ATP, incorporated by the reverse transcriptase. Other methods, i.e., quantitative immunoassay, may also be useful.

Still another embodiment of this invention is a method for treating an HTLV-III virus-related disease in a subject. The method comprises administering to the patient a suitable amount of a physiologically acceptable HTLV-III reverse transcriptase inhibiting substance for a suitable period.

The substance may be administered by a variety of methods, including injection in a pharmaceutically acceptable carrier, i.e. intravenously or peritoneally, topical application, oral application in a liquid or solid form or a variety of other routes well known in the art.

EXPERIMENTAL DETAILS

Figure 1:
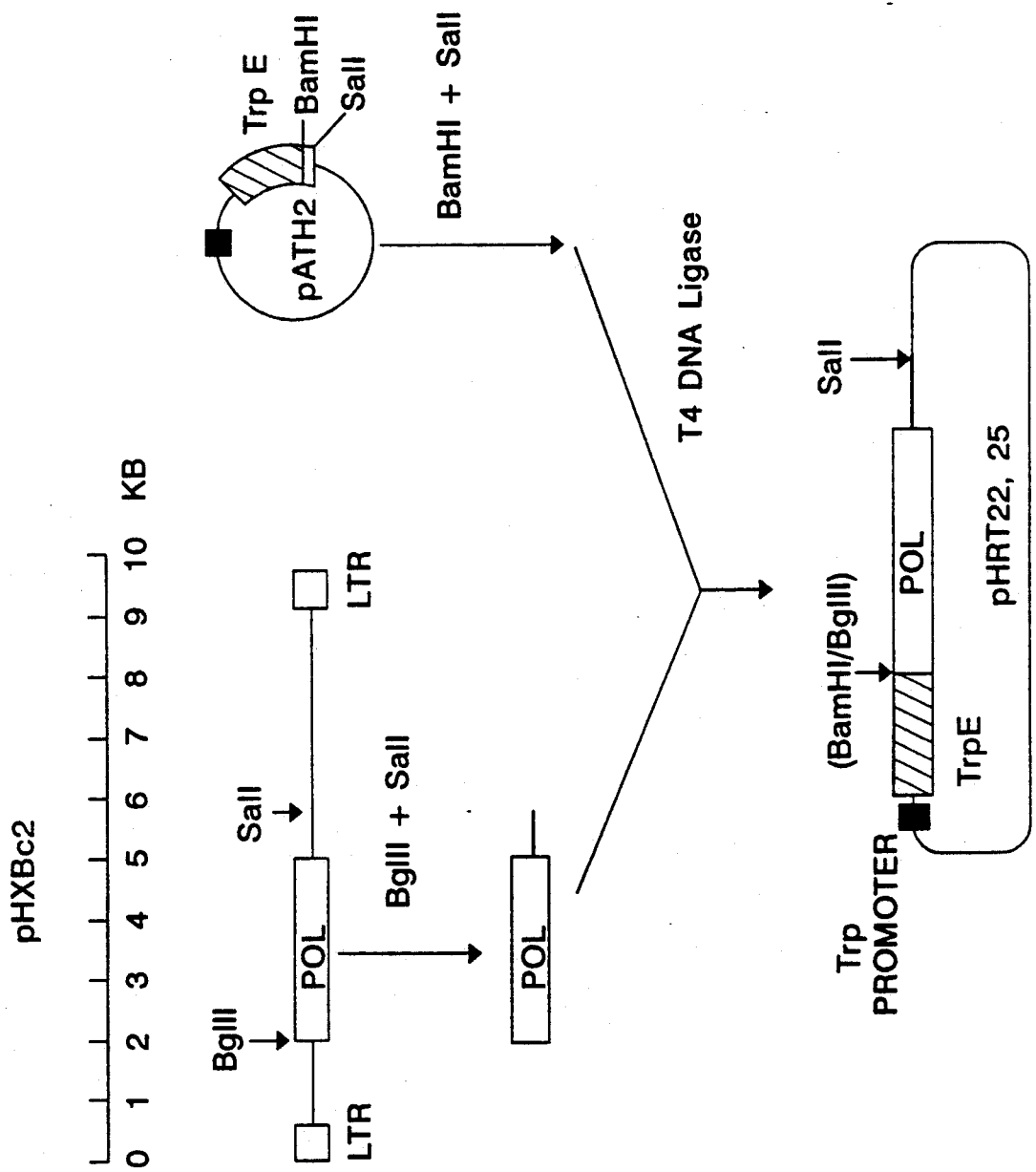
FIG. 1. Construction of active gene fusion.

To facilitate the preparation of the HTLV-III enzyme, gene fusions have been prepared between the trpE gene of *E. coli* and the appropriate portion of the viral pol gene. A large DNA fragment that contains almost all of the pol gene was excised from a biologically active proviral clone (pHXBc2; (12)) and inserted into the pATH2 expression vector (13) by fusion of the 5' half of the trpE gene to the pol sequences in the correct reading frame (FIG. 1). Two duplicate clones of the resulting plasmids, pHRT22 and pHRT25, were selected for analysis. A detailed restriction map of one of the clones, pHRT25, is shown in FIG. 2. Clones pHRT22 and pHRT25 have essentially similar restriction maps. Parallel constructions were performed to insert the same pol sequences into the pATH3 vector in the wrong reading frame to form the control plasmids pHRT31 and pHRT32.

Bacterial cultures containing various plasmids were grown in minimal medium, starved for tryptophan, and exposed to indoleacrylic acid to derepress the trp operon (14–17). After 2h, the cells were harvested, lysates were prepared, and the crude extracts were assayed directly for reverse transcriptase activity (FIG. 3A) as described previously (16–18). The extracts were tested for their ability to incorporate the appropriate radioactive triphosphate on either of two substrates: poly(rA) primed with oligo(dT), or poly(rC) primed with oligo (dG). Each substrate was tested with either of two divalent cations: $Mg^{++}$ (10 mM), or $Mn^{++}$ (1 mM).

All the cultures, no matter what plasmids they carried, showed considerable background activity on the poly(rA): oligo(dT) substrate; only a slightly higher level of activity was apparent from cells carrying the pHRT22 and pHRT25 constructs. In contrast, assays on the poly(rC): oligo(dG) substrate gave a dramatic result. Cells carrying the vector DNA showed essentially no background activity, while cells containing pHRT22 and pHRT25 yielded high levels of activity (FIG. 3, panel A, row 2). The activity was highly specific for $Mg^{++}$ as the divalent cation (compare rows 2, 4). This behavior was distinct from the activity of the murine reverse transcriptase, which is most active on the poly(A): oligo(dT) template with $Mn^{++}$ (column V). Control plasmids formed with fusions out of frame showed a trace of activity, only slightly above background.

In an attempt to reduce the background of DNA polymerase activity on the poly(rA): oligo(dT) template, the plasmids were transferred into a bacterial strain deficient in DNA Polymerase I (18). These cells do not support replication of the plasmid DNA, and transformants carry the plasmid DNA integrated into the host chromosome only in one or a few copies. Extracts were prepared and assayed as before (FIG. 3B).

PolyA$^-$ cells carrying the vector plasmid pATH2 showed no detectable background activity on either template, with either divalent cation. These same cells carrying the pHRT22 construct showed high levels of activity in the presence of Mg++; the activity could be detected on either poly(rC):oligo(dG) or on poly(rA):oligo(dT), but there was slightly higher activity on the poly(rC):oligo(dG) template. There was very little activity in the presence of Mn++ on either template. These properties of the activity duplicate precisely the behavior of the authentic HTLV-III reverse transcriptase enzyme as purified from virion particles (9-11).

To obtain a quantitative measure of the level of activity, assays were repeated on poly(rC):oligo(dG) template with Mg++, and the amount of incorporated radioactivity was determined by scintillation counting. Assays lacking either primer or template showed only background activity (data not shown). Titration of the extracts in reactions allowed to proceed for 10 min showed that the assay was linear with up to 1 ul of extract (Table 1).

Extracts of cells carrying the pHRT22 constructs showed more than a 200-fold increase in specific activity over extracts from control cells. Analysis of the time course of the reaction, using 0.1 ul of extract, showed that the reaction was linear for more than 10 minutes (Table 2). These experiments also showed large increases in the specific activity of cells carrying the pHRT22 constructs relative to controls. The PolA− cells with pHRT22 yielded about 5-fold less activity that the PolA+ cells carrying the same plasmid, presumably due to the lower copy number of the plasmids in the PolA− cells.

In conclusion, the HTLV-III pol gene has been inserted into a bacterial expression plasmid and it was demonstrated that the construct induces reverse transcriptase activity. The appearance of activity depends on the joining of the trpE and pol sequences in the correct reading frame, and is independent of the bacterial polA gene. The resulting activity closely mimics the behavior of the authentic HTLV-III enzyme, strongly preferring Mg++ over Mn++, and differs sharply from the enzyme encoded by the murine leukemia viruses. It is expected that these constructs and more active derivatives will be useful in the genetic analysis of the functions of the HTLV-III pol gene, and in surveys for antiviral agents.

TABLE 1

| | Titration of Extracts | | |
|---|---|---|---|
| Cell line | Volume of Extract (μl) | dGTP incorporated (pmol/10 min) | specific activity (pmol/10 min/ μg protein) |
| HB101(pATH2) | 0 | 0 | |
| | 0.2 | <0.035 | |
| | 0.06 | <0.035 | |
| | 0.1 | <0.035 | ≦0.02 |
| | 0.3 | <0.035 | |
| | 1.0 | <0.035 | |
| HB101(pHRT22) | 0 | 0 | |
| | 0.02 | 0.6 | |
| | 0.06 | 0.8 | |
| | 0.1 | 1.9 | 4.3 ± 0.07 |
| | 0.3 | 4.2 | |
| | 1.2 | 14.1 | |

Legend
Extracts from the indicated cultures were prepared as before (16-17). The indicated volumes of the extracts were incubated in reaction mixes (50 μl total volume) containing 50 mM Tris-HCl pH 8.3, 20 mM DTT, 60 mM NaCl, 0.05% NP40, 10 mM MgCl$_2$, 10 μg/ml poly (rC), 5 μg/ml oligo(dG), and 10 μM a$^{-32}$P-dGTP (1 Ci/mmole).
Reactions were carried out for 10 min at 37° C. The reaction mix was spotted on squares of DEAE paper, the papers were batch-washed in 2 X SSC, rinsed in ethanol and dried, and the incorporated counts were measured by scintillation counting. Background counts of 220 CPM present in reactions without extracts were subtracted before calculation of the pmoles of nucleotide incorporated. Protein determinations, performed by the method of Bradford (19), gave concentrations for HB101 (pATH2): 4.4 mg/ml; and HB101(pHRT22): 3.3 mg/ml. The specific activity of the extracts was calculated from the slope of a least squares fit of the titration data.

TABLE 2

| | Time Course of Incorporation | | |
|---|---|---|---|
| Cell in | Time (min) | dGTP incorporated (pmol/μg protein) | specific (pmol/μg protein/10 min) |
| HB101(pATH2) | 0 | 0 | |
| | 1 | <0.1 | |
| | 5 | <0.1 | |
| | 10 | <0.1 | ≦0.05 |
| | 20 | <0.1 | |
| | 40 | <0.1 | |
| HB101(pHRT22) | 0 | 0 | |
| | 1 | 0.4 | |
| | 2 | 0.4 | |
| | 5 | 1.1 | 1.7 ± 0.1 |
| | 10 | 2.1 | |
| | 20 | 3.5 | |
| | 40 | 6.5 | |
| C2110(pATH2) | 0 | 0 | |
| | 1 | <0.07 | |
| | 2 | <0.07 | |
| | 5 | <0.07 | ≦0.03 |
| | 10 | <0.07 | |
| | 20 | <0.07 | |
| | 40 | <0.07 | |
| C2110(pHRT22) | 0 | 0 | |
| | 1 | 0.004 | |
| | 2 | 0.06 | 0.30 ± 0.03 |
| | 5 | 0.2 | |
| | 10 | 0.2 | |
| | 20 | 0.6 | |
| | 40 | 1.2 | |

Legend
0.1 μl of crude extracts from the indicated cultures were incubated in reaction mixes for the indicated times, and the incorporated counts were determined as in Table 1. Background activity of 150-200 CPM were substracted before calculating activities. Protein concentrations were as follows. HB101(pATH2): 4.4 mg/ml; HB101(pHRT22): 3.3 mg/ml; C2110(pATH2): 3.9 mg/ml; C2110(pHRT22): 5.2 (mg/ml). Specific activities were determined as before.

References

1. R. C. Gallo et al., *Science* 220, 865 (1983).
2. F. Barre-Sinoussi et al., *Science* 220, 868 (1983).
3. R. C. Gallo et al., *Science* 224, 500 (1984).
4. A. S. Fauci et al., *Ann. Intern. Med.* 100, 92 (1984).
5. P. Chandra, *Top. Curr. Chem.* 52, 99 1974).
6. E. DeClercq, *Cancer Lett.* 8, 9 (1979).
7. J. B. McCormick et al., *Lancet II*, 1367 (1984).
8. H. Mitsuya et al., *Science* 226, 172 (1984).
9. M. A. Rey, B. Spire, D. Dormont, F. Barre-Sinoussi, L. Montagnier, and J. C. Chermann, *Biochem. Biophys. Res. Commun.* 121, 126 (1984).
10. P. Chandra, A. Vogel, and T. Gerber, *Cancer Res. (Suppl.)* 45, 4677s (1985).

11. A. D. Hoffman, B. Banapour, and J. A., Levy, *Virology* 147, 326 (1985).

12. L. Ratner et al., *Nature* 313, 277 (1985).

13. T. J. Koerner, Duke University; unpublished.

14. K. R. Spindler et al., *J. Virol.* 49, 132 (1984).

15. D. G. Kleid et al., *Science* 214, 1125 (1981).

16. N. Tanese, M. Roth, and S. P. Goff, *Proc. Natl. Acad. Sci. USA* 82, 4944 (1985).

17. M. Roth, N. Tanese, and S. P. Goff, *J. Biol. Chem.* 260,9326 (1985).

18. S. P. Goff, P. Traktman, and D. Baltimore, *J. Virol.* 38, 239 (1981).

19. M. M. Bradford, *Anal. Biochem.* 72, 248 (1976).

What is claimed is:

1. A method for producing a polypeptide having HTLV-III reverse transcriptase activity, the activity being higher in the presence of $Mg^{++}$ than in the presence of $Mn^{++}$, which comprises (a) growing *E. coli* host cells containing a plasmid designated pHRT25 (ATCC Accession No. 67117), which plasmid consists essentially of DNA encoding the polypeptide under the control of the trp promoter, and about half of the trp E gene, in minimal medium, (b) starving for tryptophan, (c) exposing the cells so starved to indoleacrylic acid so as to derepress the trp promoter and thereby permit expression of the polypeptide in the cells, and (d) recovering the polypeptide from the cells.

* * * * *